(12) United States Patent
Croteau et al.

(10) Patent No.: US 8,426,684 B2
(45) Date of Patent: Apr. 23, 2013

(54) ISOLATED MENTHONE REDUCTASE AND NUCLEIC ACID MOLECULES ENCODING SAME

(75) Inventors: Rodney B. Croteau, Newport, OR (US);
Edward M. Davis, Pullman, WA (US);
Kerry L. Ringer, Richland, WA (US)

(73) Assignee: Washington State University Research Foundation, Pullman, WA (US)

( * ) Notice: Subject to any disclaimer, the term of this patent is extended or adjusted under 35 U.S.C. 154(b) by 1194 days.

(21) Appl. No.: 11/569,493

(22) PCT Filed: Jun. 15, 2004

(86) PCT No.: PCT/US2004/018908
§ 371 (c)(1),
(2), (4) Date: Aug. 5, 2009

(87) PCT Pub. No.: WO2006/001802
PCT Pub. Date: Jan. 5, 2006

(65) Prior Publication Data
US 2009/0300801 A1    Dec. 3, 2009

(51) Int. Cl.
*C12N 15/29* (2006.01)
*C12N 15/52* (2006.01)
*C12N 15/82* (2006.01)

(52) U.S. Cl.
USPC .................. 800/298; 536/23.2; 435/282.35; 435/320.1; 435/419

(58) Field of Classification Search .................. 536/23.2
See application file for complete search history.

(56) References Cited

PUBLICATIONS

McConkey et al. Plant Physiology (Jan. 2000), vol. 122; pp. 215-223.*
Kjonaas, R. et al. Plant Physiology (1982) vol. 69, pp. 1013-1017.*
Davis, E et al. Plant Physiology (2005), vol. 137, pp. 873-881.*
Krasnyanski, S., et al., "Transformation of the Limonene Synthase Gene Into Peppermint (*Mentha piperita* L.) and Preliminary Studies on the Essential Oil Profiles of Single Transgenic Plants," Theoretical and Applied Genetics 99:676-682, 1999.
Ringer, K.L., et al., "Monoterpene Double-Bond Reductases of the (−)-Menthol Biosynthetic Pathway: Isolation and Characterization of cDNAs Encoding (−)-Isopiperitenone Reductase and (+)-Pulegone Reductase of Peppermint," Archives of Biochemistry and Biophysics 418:80-92, 2003.
Sato, H., et al., "Production of an Interspecific Somatic Hybrid Between Peppermint and Gingermint," Plant Science 115:101-107, 1996.

\* cited by examiner

*Primary Examiner* — Russell Kallis
(74) *Attorney, Agent, or Firm* — Christensen O'Connor Johnson Kindness PLLC

(57) ABSTRACT

The present invention provides isolated menthone reductase proteins, isolated nucleic acid molecules encoding menthone reductase proteins, methods for expressing and isolating menthone reductase proteins, and transgenic plants expressing elevated levels of menthone reductase protein.

15 Claims, No Drawings

US 8,426,684 B2

ISOLATED MENTHONE REDUCTASE AND NUCLEIC ACID MOLECULES ENCODING SAME

STATEMENT OF GOVERNMENT LICENSE RIGHTS

This invention was made, at least in part, with government support under Grant No. DE-FG03-99ER20212 awarded by the United States Department of Energy. The government may have certain rights in the invention.

CROSS-REFERENCE TO RELATED APPLICATION

This application is the National Stage of International Application No. PCT/US2004/18908, filed on Jun. 15, 2004.

FIELD OF THE INVENTION

This invention relates to isolated menthone reductase proteins, to nucleic acid molecules encoding menthone reductase proteins, to methods for expressing and isolating menthone reductase proteins, and to transgenic mint plants expressing elevated levels of menthone reductase proteins.

BACKGROUND OF THE INVENTION

The essential oil of peppermint (Mentha×piperita) is composed principally of C3-oxygenated p-menthane monoterpenes, and the characteristic organoleptic properties of this oil are derived predominantly from (−)-menthol. Menthol biosynthesis begins with the diversion of the primary isoprenoid intermediates, isopentenyl diphosphate and its allylic isomer, dimethylallyl diphosphate, to geranyl diphosphate (the precursor of all monoterpenes) by the prenyltransferase geranyl diphosphate synthase (GPPS), and is followed by ionization and cyclization of this $C_{10}$ intermediate to limonene by the terpene cyclase (−)-(4S)-limonene synthase. Regiospecific and stereospecific hydroxylation of this monoterpene olefin intermediate is catalyzed by cytochrome P450 limonene-3-hydroxylase to yield (−)-trans-isopiperitenol, and is followed by dehydrogenation of this allylic alcohol (by isopiperitenol dehydrogenase) to afford the α,β-unsaturated ketone (−)-isopiperitenone. The endocyclic double bond of this intermediate is reduced by isopiperitenone reductase to yield (+)-cis-isopulegone, which undergoes enzymatic isomerization of the isopropenyl double bond ($\Delta^{8,9}$) to yield the conjugated ketone (+)-pulegone ($\Delta^{4,8}$). The newly formed isopropylidene double bond is reduced by pulegone reductase to yield (−)-menthone and lesser amounts of (+)-isomenthone. Alternatively, in a cytochrome P450-mediated side-reaction, pulegone undergoes C9 hydroxylation and intramolecular cyclization and dehydration to yield (+)-menthofuran. In the final reductive step of the pathway, (−)-menthone and (+)-isomenthone are reduced to (−)-menthol and (+)-neoisomenthol, respectively, or, by a separate reductase, to (+)-neomenthol and (+)-isomenthol, respectively; the latter three monoterpenol isomers are minor constituents of peppermint oil.

Monoterpene biosynthesis in peppermint occurs in the highly specialized secretory cells of epidermal oil glands, and recent evidence suggests this metabolic process is divided into two temporally distinct periods of transcriptional and translational activity. The initial process is characterized by the de novo biosynthesis of the p-menthane monoterpenes (as determined by $^{14}CO_2$ incorporation) which results in the accumulation of mostly (−)-menthone. In vitro assay of the relevant enzymes of menthone biosynthesis demonstrated that these activities appear coincidentally during leaf expansion, and endure for a brief time period (12-20 days post leaf initiation) with peak activity levels correlating with the essential oil secretion (gland filling) phase of gland development. RNA-blot analysis further showed that maximum transcript accumulation of limonene synthase occurs immediately prior to maximal enzyme activity, suggesting that at least the first committed enzyme of monoterpene biosynthesis is transcriptionally regulated. However, the production of (−)-menthol from menthone is not significant until late in leaf development, after de novo monoterpene biosynthesis is essentially complete; this process occurs in mature oil gland cells during the post-secretory phase. This second developmental process, termed "oil maturation", is characterized by the depletion of the dominant intermediate menthone, and is concomitant with increased activity of the menthone reductases and the accumulation of menthol (and lesser amounts of the epimer neomenthol).

The present invention provides isolated nucleic acid molecules (e.g., cDNA molecules) that encode menthone: (3R)-(−)-menthol reductase that converts (−)-menthone to (3R)-(−)-menthol. The present invention also provides isolated menthone: (3R)-(−)-menthol reductase proteins.

SUMMARY OF THE INVENTION

In one aspect, the present invention provides isolated nucleic acid molecules that encode a menthone: (3R)-(−)-menthol reductase and that hybridize to the complement of the nucleic acid molecule having the nucleic acid sequence set forth in SEQ ID NO:1 under hybridization conditions of 5×SSC at 42° C. for 12 hours, followed by wash conditions of 5×SSC at 42° C. for 1 hour. The nucleic acid molecule having the nucleic acid sequence set forth in SEQ ID NO:1 is a cDNA molecule that encodes the peppermint menthone: (3R)-(−)-menthol reductase having the amino acid sequence set forth in SEQ ID NO:2.

In another aspect, the present invention provides replicable expression vectors that include a nucleic acid molecule that encodes a menthone: (3R)-(−)-menthol reductase wherein the nucleic acid molecule hybridizes to the complement of SEQ ID NO:1 under hybridization conditions of 5×SSC at 42° C. for 12 hours, followed by wash conditions of 5×SSC at 42° C. for 1 hour.

In another aspect, the present invention provides host cells (e.g., plant cells) that include an expression vector that comprises a nucleic acid molecule that encodes a menthone: (3R)-(−)-menthol reductase and that hybridizes to the complement of SEQ ID NO:1 under hybridization conditions of 5×SSC at 42° C. for 12 hours, followed by wash conditions of 5×SSC at 42° C. for 1 hour.

In another aspect, the present invention provides transgenic plants (e.g., transgenic mint plants) that include an expression vector that includes a nucleic acid molecule that encodes a menthone: (3R)-(−)-menthol reductase, wherein the nucleic acid molecule hybridizes to the complement of SEQ ID NO:1 under hybridization conditions of 5×SSC at 42° C. for 12 hours, followed by wash conditions of 5×SSC at 42° C. for 1 hour.

In another aspect, the present invention provides methods of increasing the amount of a menthone: (3R)-(−)-menthol reductase in a host cell (e.g., plant cell). The methods of this aspect of the invention include the step of introducing into a host cell an expression vector that includes a nucleic acid molecule that hybridizes to the complement of SEQ ID NO:1 under hybridization conditions of 5×SSC at 42° C. for 12 hours, followed by wash conditions of 5×SSC at 42° C. for 1 hour, under conditions that enable expression of the nucleic acid molecule to produce menthone: (3R)-(−)-menthol reductase in the host cell.

In another aspect, the present invention provides isolated menthone: (3R)-(−)-menthol reductase proteins that are at least 70% identical to the amino acid sequence set forth in SEQ ID NO:2.

The isolated nucleic acid molecules and vectors of the invention can be used, for example, to express menthone: (3R)-(−)-menthol reductase in host cells, or in transgenic organisms, such as transgenic mint plants (e.g., transgenic peppermint plants). For example, isolated nucleic acid molecules of the invention can be used to construct expression vectors of the invention, and the expression vectors can be introduced into mint plant cells. Transgenic mint plants can be regenerated from the transgenic mint plant cells. The transgenic mint plants express elevated levels of menthone: (3R)-(−)-menthol reductase and, consequently, produce elevated amounts of (−)-menthol which is a desirable component of mint essential oil that is used in flavors and fragrances. The (−)-menthol can be extracted from the transgenic mint plants. The isolated proteins of the invention can be used, for example, for the biocatalytic conversion, in vitro, of menthone to menthol which can be used, for example, as a flavoring agent in foodstuffs. The isolated proteins of the invention can also be used, for example, to further characterize the physical and/or enzymatic characteristics of menthone: (3R)-(−)-menthol reductase, and, by mutation, to create menthone: (3R)-(−)-menthol reductases having desirable enzymatic characteristics.

The methods of the invention for increasing the amount of a menthone: (3R)-(−)-menthol reductase in a host cell are useful, for example, for expressing elevated levels of menthone: (3R)-(−)-menthol reductase in cultured mint cells. The transgenic, cultured, mint cells produce elevated amounts of (−)-menthol.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual,* 2nd ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

As used herein, the term "menthone: (3R)-(−)-menthol reductase" refers to an enzyme that is capable of converting (−)-menthone to (3R)-(−)-menthol, and that is also capable of converting (+)-isomenthone to (3R)-(+)-neoisomenthol. The primary product of menthone: (3R)-(−)-menthol reductase, using (−)-menthone as the substrate, is (3R)-(−)-menthol. Typically, at least 80% of the product produced by menthone: (3R)-(−)-menthol reductase from (−)-menthone is (3R)-(−)-menthol. The primary product of menthone: (3R)-(−)-menthol reductase, using (+)-isomenthone as the substrate, is (3R)-(+)-neoisomenthol. Typically, at least 80% of the product produced by menthone: (3R)-(−)-menthol reductase from (+)-isomenthone is (3R)-(+)-neoisomenthol.

As used herein, the term "mint plant" refers to a plant of the genus *Mentha* (e.g., *M. piperita, M. spicata,* and *M. orvensis*).

The terms "replicable expression vector" and "expression vector" refer to a piece of DNA, usually double-stranded, which may have inserted into it another piece of DNA (the insert DNA) such as, but not limited to, a cDNA molecule. The vector is used to transport the insert DNA into a suitable host cell. The insert DNA may be derived from the host cell, or may be derived from a different cell or organism. Once in the host cell, the vector can replicate independently of or coincidental with the host chromosomal DNA, and several copies of the vector and its inserted DNA may be generated. Replicable expression vectors and expression vectors include the necessary elements that permit transcribing and translating the insert DNA into a polypeptide. Many molecules of the polypeptide encoded by the insert DNA can thus be rapidly synthesized. The terms "replicable expression vector" and "expression vector" include a T-DNA that is integrated into a plant genome and that includes an insert (e.g., a DNA molecule encoding a menthone: (3R)-(−)-menthol reductase) that is operably associated with the necessary elements that permit transcribing and translating the insert DNA to produce the encoded protein.

In one aspect, the present invention provides isolated nucleic acid molecules that each encode a menthone: (3R)-(−)-menthol reductase and that hybridize to the complement of the nucleic acid molecule having the sequence set forth in SEQ ID NO:1 under hybridization conditions of 5×SSC at 42° C. for 12 hours, followed by wash conditions of 5×SSC at 42° C. for 1 hour. Some isolated nucleic acid molecules of the present invention hybridize to the complement of the nucleic acid molecule having the sequence set forth in SEQ ID NO:1 under hybridization conditions of 5×SSC at 55° C. for 12 hours, followed by wash conditions of 5×SSC at 55° C. for 1 hour. Some isolated nucleic acid molecules of the present invention hybridize to the complement of the nucleic acid molecule having the sequence set forth in SEQ ID NO:1 under hybridization conditions of 5×SSC at 65° C. for 12 hours, followed by wash conditions of 5×SSC at 65° C. for 1 hour. Guidance for designing and conducting nucleic acid hybridization experiments is provided, for example, in Sambrook et al., supra, pp. 11.45-11.61, which portion of the Sambrook et al. laboratory manual is incorporated herein by reference. The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The isolated nucleic acid molecules of the present invention can be any type of nucleic acid molecules, including cDNA and genomic DNA molecules. cDNAs of the present invention can be cloned, for example, by using the technique of hybridizing radiolabelled nucleic acid probes to nucleic acids immobilized on nitrocellulose filters or nylon membranes, as set forth, for example, at pages 9.52 to 9.55 of *Molecular Cloning, A Laboratory Manual* (2nd edition), J. Sambrook et al. eds., the cited pages of which are incorporated herein by reference.

For example, a cDNA of the present invention can be cloned by screening a mint plant oil gland cDNA library (made from mRNA extracted from mint plant oil glands at the appropriate stage of development, as described in Example 1) with the complement of the cDNA of SEQ ID NO:1 using the technique of nucleic acid hybridization. By way of non-limiting example, exemplary hybridization and wash conditions useful for screening the oil gland cDNA library are as follows. Hybridization in 5×SSC, 1% sodium dodecyl sulfate, at 42° C. for 16 hours. Exemplary very high stringency wash conditions for screening the oil gland cDNA library are: two washes of fifteen minutes each at 20° C. to 30° C. in 5.0×SSC, followed by two washes of twenty minutes each at 65° C. in 5.0×SSC. Exemplary high stringency wash conditions for screening the oil gland cDNA library are: two washes of twenty minutes each at 20° C. to 30° C. in 5.0×SSC, followed by one wash of thirty minutes at 55° C. in 5.0×SSC. Exemplary moderate stringency wash conditions for screening the oil gland cDNA library are: two washes of twenty minutes each at 20° C. to 30° C. in 5.0×SSC, followed by one wash of thirty minutes at 42° C. in 5.0×SSC.

Genomic DNA molecules of the present invention can be isolated, for example, by using the complement of the DNA molecule, having the sequence set forth in SEQ ID NO:1, as a hybridization probe to screen a genomic library using the aforementioned technique of hybridizing radiolabelled nucleic acid probes to nucleic acids immobilized on nitrocellulose filters or nylon membranes. By way of non-limiting example, exemplary hybridization and wash conditions are: hybridization at 50° C. in 5.0×SSC, 1% sodium dodecyl sulfate; washing (three washes of twenty minutes each at 50° C.) in 5.0×SSC, 1% (w/v) sodium dodecyl sulfate.

Hybridization probes may be labeled with appropriate reporter molecules. Means for producing specific hybridization probes include oligolabeling, nick translation, end-labeling or PCR amplification using a labeled nucleotide.

Again, by way of example, nucleic acid molecules of the present invention can be isolated by the polymerase chain reaction (PCR) described in *The Polymerase Chain Reaction* (Mullis et al. eds.), Birkhauser Boston (1994), incorporated herein by reference. Thus, for example, first strand DNA synthesis can be primed using an oligo(dT) primer, and second strand cDNA synthesis can be primed using an oligonucleotide primer that corresponds to a portion of the 5'-untranslated region of a cDNA molecule that is homologous to the target DNA molecule. Subsequent rounds of PCR can be primed using the second strand cDNA synthesis primer and a primer that corresponds to a portion of the 3'-untranslated region of a cDNA molecule that is homologous to the target DNA molecule. In this way, homologs of a cDNA molecule can be cloned from a range of different plant species.

By way of non-limiting example, representative PCR reaction conditions for amplifying nucleic acid molecules of the present invention (such as amplifying genes from plant genomic DNA) are as follows. The following reagents are mixed in a tube (on ice) to form the PCR reaction mixture: DNA template (e.g., up to 1 µg genomic DNA, or up to 0.1 µg cDNA), 0.1-0.3 mM dNTPs, 10 µl 10×PCR buffer (10×PCR buffer contains 500 mM KCl, 1.5 mM $MgCl_2$, 100 mM Tris-HCl, pH 8.3), 50 pmol of each PCR primer (PCR primers should preferably be greater than 20 bp in length and have a degeneracy of $10^2$ to $10^3$), 2.5 units of Taq DNA polymerase (Perkin Elmer, Norwalk, Conn.) and deionized water to a final volume of 50 µl. The tube containing the reaction mixture is placed in a thermocycler and a thermocycler program is run as follows. Denaturation at 94° C. for 2 minutes, then 30 cycles of: 94° C. for 30 seconds, 47° C. to 55° C. for 30 seconds, and 72° C. for 30 seconds to two and a half minutes.

Further, nucleic acid molecules of the present invention can also be isolated, for example, by utilizing antibodies that recognize the protein encoded by the nucleic acid molecule. By way of non-limiting example, a cDNA expression library can be screened using antibodies in order to identify one or more clones that encode a protein recognized by the antibodies. DNA expression library technology is well known to those of ordinary skill in the art. Screening cDNA expression libraries is fully discussed in Chapter 12 of Sambrook et al. (1989) *Molecular Cloning: A Laboratory Manual*, 2nd ed., Cold Spring Harbor Laboratory, Cold Spring Harbor, N.Y., the cited chapter of which is incorporated herein by reference.

By way of representative example, antigen useful for raising antibodies for screening expression libraries can be prepared in the following manner. A full-length cDNA molecule of the present invention (or a cDNA molecule of the invention that is not full-length, but which includes all of the coding region) can be cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the protein encoded by the cDNA is expressed in *E. coli* and then purified. For example, *E. coli* XL1-Blue harboring a Bluescript vector including a cDNA molecule of interest can be grown overnight at 37° C. in LB medium containing 100 µg ampicillin/ml. A 50 µl aliquot of the overnight culture can be used to inoculate 5 ml of fresh LB medium containing ampicillin, and the culture grown at 37° C. with vigorous agitation to $A_{600}=0.5$ before induction with 1 mM IPTG. After an additional two hours of growth, the suspension is centrifuged (1000×g, 15 min, 4° C.), the media removed, and the pelleted cells resuspended in 1 ml of cold buffer that preferably contains 1 mM EDTA and one or more proteinase inhibitors, such as those described herein in connection with the purification of the isolated proteins of the present invention. The cells can be disrupted by sonication with a microprobe. The chilled sonicate is cleared by centrifugation and the expressed, recombinant protein purified from the supernatant by art-recognized protein purification techniques, such as those described herein.

Methods for preparing monoclonal and polyclonal antibodies are well known to those of ordinary skill in the art and are set forth, for example, in chapters five and six of *Antibodies A Laboratory Manual*, E. Harlow and D. Lane, Cold Spring Harbor Laboratory (1988), the cited chapters of which are incorporated herein by reference.

Nucleic acid molecules of the present invention can be used for a variety of purposes including, but not limited to, the expression of menthone: (3R)-(−)-menthol reductase in bacterial and/or yeast cells in the presence of (−)-menthone to produce (3R)-(−)-menthol; and production of genetically modified mint plants that express an elevated level of menthone: (3R)-(−)-menthol reductase in the oil gland cells and so produce larger amounts of (3R)-(−)-menthol.

In another aspect, the present invention provides replicable expression vectors that each include a nucleic acid molecule that encodes a menthone: (3R)-(−)-menthol reductase and that hybridizes to the complement of the nucleic acid molecule having the sequence set forth in SEQ ID NO:1 under hybridization conditions of 5×SSC at 42° C. for 12 hours, followed by wash conditions of 5×SSC at 42° C. for 1 hour. Some replicable expression vectors of the invention include a nucleic acid molecule that encodes a menthone: (3R)-(−)-menthol reductase and hybridizes to the complement of the nucleic acid molecule having the sequence set forth in SEQ ID NO:1 under hybridization conditions of 5×SSC at 55° C. for 12 hours, followed by wash conditions of 5×SSC at 55° C. for 1 hour. Some replicable expression vectors of the invention include a nucleic acid molecule that encodes a menthone: (3R)-(−)-menthol reductase and hybridizes to the complement of the nucleic acid molecule having the sequence set forth in SEQ ID NO:1 under hybridization conditions of 5×SSC at 65° C. for 12 hours, followed by wash conditions of 5×SSC at 65° C. for 1 hour.

The replicable expression vectors of the invention can include transcriptional and translational regulatory sequences. In general, the transcriptional and translational regulatory sequences may include, but are not limited to, promoter sequences, ribosomal binding sites, transcriptional start and stop sequences, translational start and stop sequences, and enhancer or activator sequences. Promoter sequences may be, for example, constitutive or inducible promoters. The promoters may be, for example, naturally-occurring promoters or hybrid promoters. Hybrid promoters, which combine elements of more than one promoter, are also known in the art.

A replicable expression vector may comprise additional elements. For example, the replicable expression vector may have two replication systems, thus allowing it to be maintained in two organisms, for example in mammalian or insect cells for expression and in a prokaryotic host for cloning and amplification. Furthermore, for integrating expression vectors (that integrate into a genome by homologous recombination), the expression vector contains at least one sequence homologous to a sequence in the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

In addition, a replicable expression vector typically contains a selectable marker gene to allow the selection of transformed host cells. Selection genes are well known in the art and will vary with the host cell used.

The vectors of the invention can be any type of vector, including plasmid vectors (such as vectors based on the Ti plasmid of *Agrobacterium tumefaciens*), and viral vectors. Specific, representative, examples of prokaryotic and eukaryotic vectors are provided throughout the present application in the context of the in vivo expression of menthone: (3R)-(−)-menthol reductase, and the cloning and manipulation of nucleic acid molecules encoding menthone: (3R)-(−)-menthol reductase.

The vectors of the invention can be used, for example, to express menthone: (3R)-(−)-menthol reductase in isolated host cells, in cultured host cells or tissue, or in transgenic organisms, such as transgenic mint plants. For example, Ti-based vectors of the invention can be used to integrate a nucleic acid molecule encoding a menthone: (3R)-(−)-menthol reductase into the genome of a peppermint plant. The nucleic acid molecule encoding a menthone: (3R)-(−)-menthol reductase may be under the control of a promoter, and optionally other transcriptional control elements, that direct expression of the nucleic acid molecule encoding a menthone: (3R)-(−)-menthol reductase in a desired temporal and/or spatial pattern. For example, the CAMV 35S promoter can be used to express a nucleic acid molecule encoding a menthone: (3R)-(−)-menthol reductase in mint oil gland cells.

In another aspect, the present invention provides host cells that each include an expression vector that includes a nucleic acid sequence that encodes a menthone: (3R)-(−)-menthol reductase. The nucleic acid sequence that encodes a menthone: (3R)-(−)-menthol reductase hybridizes to the complement of SEQ ID NO:1 under hybridization conditions of 5×SSC at 42° C. for 12 hours, followed by wash conditions of 5×SSC at 42° C. for 1 hour. Some host cells of the present invention include an expression vector that includes a nucleic acid sequence that encodes a menthone: (3R)-(−)-menthol reductase, and that hybridizes to the complement of SEQ ID NO:1 under hybridization conditions of 5×SSC at 55° C. for 12 hours, followed by wash conditions of 5×SSC at 55° C. for 1 hour. Some host cells of the present invention include an expression vector that includes a nucleic acid sequence that encodes a menthone: (3R)-(−)-menthol reductase, and that hybridizes to the complement of SEQ ID NO:1 under hybridization conditions of 5×SSC at 65° C. for 12 hours, followed by wash conditions of 5×SSC at 65° C. for 1 hour.

The host cells of the invention can be any type of living cell, such as prokaryotic cells or eukaryotic cells, including yeast cells and plant cells. Vectors of the invention can be introduced into plant cells using techniques well known to those skilled in the art. These methods include, but are not limited to, (1) direct DNA uptake, such as particle bombardment or electroporation (see, Klein et al., *Nature* 327:70-73, 1987; U.S. Pat. No. 4,945,050), and (2) *Agrobacterium*-mediated transformation (see, e.g., U.S. Pat. Nos. 6,051,757; 5,731, 179; 4,693,976; 4,940,838; 5,464,763; and 5,149,645, each of which patents are incorporated herein by reference). Within the cell, the transgenic sequences may be incorporated within the chromosome.

Nucleic acid molecules (including vectors of the present invention) can be introduced into cultured mammalian host cells, and other host cells that do not have rigid cell membrane barriers, for example by using the calcium phosphate method as originally described by Graham and Van der Eb (*Virology*, 52:546, 1978) and modified as described in sections 16.32-16.37 of Sambrook et al., supra. Other methods for introducing nucleic acid molecules into cells, such as Polybrene (Kawai and Nishizawa, *Mol. Cell. Biol.*, 4:1172, 1984), protoplast fusion (Schaffner, *Proc. Natl. Acad. Sci. USA*, 77:2163, 1980), electroporation (Neumann et al., *EMBO J*, 1:841, 1982), and direct microinjection into nuclei (Capecchi, *Cell*, 22:479, 1980), may also be used.

Nucleic acid molecules (including vectors of the present invention) can be introduced into prokaryotic host cells using, for example, the calcium chloride method as described in section 1.82 of Sambrook et al., supra. Electroporation may also be used. Representative prokaryote transformation techniques are set forth in Dower, W. J., in *Genetic Engineering, Principles and Methods*, 12:275-296, Plenum Publishing Corp., 1990; Hanahan et al., *Meth. Enzymol.*, 204:63, 1991.

The present invention also provides transgenic plants comprising a vector of the present invention. For example, the present invention provides transgenic plants of the genus *Mentha* (e.g., *Mentha piperita* and *Mentha spicata*) that include a vector of the present invention. Transgenic plants of the invention can be made, for example, by transferring a vector of the invention that includes a selectable marker gene, (e.g., the kan gene encoding resistance to kanamycin), into *Agrobacterium tumifaciens* containing a helper Ti plasmid as described in Hoeckema et al., *Nature*, 303:179-181, 1983, and culturing the *Agrobacterium* cells with leaf slices, or other tissues or cells, of the plant to be transformed as described by An et al., *Plant Physiology*, 81:301-305, 1986.

Transformed plant calli may be selected through the selectable marker by growing the cells on a medium containing, for example, kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition to the methods described above, several methods are known in the art for transferring nucleic acid molecules, such as vectors, into a wide variety of plant species, including gymnosperms, angiosperms, monocots and dicots (see, e.g., Glick and Thompson, eds., *Methods in Plant Molecular Biology*, CRC Press, Boca Raton, Fla. (1993), incorporated by reference herein). Representative examples include electroporation-facilitated DNA uptake by protoplasts in which an electrical pulse transiently permeabilizes cell membranes, permitting the uptake of a variety of biological molecules, including recombinant DNA (see, e.g., Rhodes et al., *Science,* 240:204-207, 1988); treatment of protoplasts with polyethylene glycol (see, e.g., Lyznik et al., *Plant Molecular Biology,* 13:151-161, 1989); and bombardment of cells with DNA-laden microprojectiles which are propelled by explosive force or compressed gas to penetrate the cell wall (see, e.g., Klein et al., *Plant Physiol.* 91:440-444, 1989; and Boynton et al., *Science,* 240(4858):1534-1538, 1988). A method that has been applied to Rye plants (*Secale cereale*) is to directly inject plasmid DNA, including a selectable marker gene, into developing floral tillers (de la Pena et al., *Nature* 325:274-276, 1987). Further, plant viruses can be used as vectors to transfer genes to plant cells. Examples of plant viruses that can be used as vectors to transform plants include the Cauliflower Mosaic Virus (see, e.g., Brisson et al., *Nature* 310:511-514, 1984). Other useful techniques include: site-specific recombination using the Cre-lox system (see, U.S. Pat. No. 5,635,381); and insertion into a target sequence by homologous recombination (see, U.S. Pat. No. 5,501,967). Additionally, plant transformation strategies and techniques are reviewed in Birch, R. G., *Ann. Rev. Plant Phys. Plant Mol. Biol.,* 48:297, 1997; and Forester et al., *Exp. Agric.,* 33:15-33, 1997.

Positive selection markers may also be utilized to identify plant cells that include a vector of the invention. For example, U.S. Pat. Nos. 5,994,629, 5,767,378, and 5,599,670, describe the use of a β-glucuronidase transgene and application of cytokinin-glucuronide for selection, and use of mannophosphatase or phosphmanno-isomerase transgene and application of mannose for selection.

The cells which have been genetically transformed and include a vector of the invention may be grown into plants by a variety of art-recognized means. See, for example, McConnick et al., *Plant Cell Reports* 5:81-84 (1986). These plants may then be grown, and either selfed or crossed with a different plant variety or line, and the resulting homozygotes or hybrids having the desired phenotypic characteristic (e.g., expression of elevated levels of menthone: (3R)-(−)-menthol reductase) identified. Two or more generations may be grown to ensure that the subject phenotypic characteristic is stably maintained and inherited and then seeds harvested to ensure the desired phenotype or other property has been achieved.

The following are representative plant species into which a vector of the invention may be introduced. The citations are to representative publications disclosing genetic transformation protocols that can be used to genetically transform the listed plant species. Tomato (U.S. Pat. No. 5,159,135); potato (Kumar, A., et al., *Plant J.* 9:821-829, 1996); tobacco (Horsch, R. B., et al., *Science* 227:1229-1231, 1985); peppermint (X. Niu et al., *Plant Cell Rep.* 17:165-171, 1998); citrus plants (Pena, L. et al., *Plant Sci.* 104:183-191, 1995); caraway (F. A. Krens, et al., *Plant Cell Rep.* 17:39-43, 1997); pineapple (U.S. Pat. No. 5,952,543). Representative transformation protocols for *Picea* species are set forth in D. H. Clapham et al., *Molecular Biology of Woody Plants* (S. M. Jain and S. C. Minocha, eds.) Vol. 2, 105-118 (2000), Kluwer Academic Publishers. A representative protocol for introducing a nucleic acid vector into peppermint cells and producing peppermint plants therefrom is set forth in Example 2 herein.

In another aspect, the present invention provides cultured plant tissue (e.g., plant tissue from a plant of the genus *Mentha*) comprising an expression vector comprising a nucleic acid molecule that encodes a menthone: (3R)-(−)-menthol reductase protein, wherein the nucleic acid molecule hybridizes to the complement of SEQ ID NO:1 under hybridization conditions of 5×SSC at 42° C. for 12 hours, followed by wash conditions of 5×SSC at 42° C. for 1 hour. In some embodiments the nucleic acid molecule hybridizes to the complement of SEQ ID NO:1 under hybridization conditions of 5×SSC at 55° C. for 12 hours, followed by wash conditions of 5×SSC at 55° C. for 1 hour. In some embodiments the nucleic acid molecule hybridizes to the complement of SEQ ID NO:1 under hybridization conditions of 5×SSC at 65° C. for 12 hours, followed by wash conditions of 5×SSC at 65° C. for 1 hour.

For example, an expression vector of the invention can be introduced into one, or more, plant cells using any of the techniques described herein for introducing nucleic acid molecules into plant cells. The plant cells can then be cultured to produce cultured plant tissue (e.g., callus) that expresses menthone: (3R)-(−)-menthol reductase. Representative, art-recognized, methods for culturing plant tissue are described, for example, in O. L. Gamborg and G. C. Phillips (Eds.) *Plant Cell, Tissue and Organ Culture: Fundamental Methods,* Springer Verlag, Berlin, 1995; and in R. D. Hall (Ed.) *Plant Cell Culture Protocols,* Humana Press, Totowa, N.J., 1999.

In another aspect, the present invention provides methods for increasing the amount of a menthone: (3R)-(−)-menthol reductase in a host cell, wherein the methods each include the step of introducing into a host cell an expression vector that includes a nucleic acid molecule, that hybridizes to the complement of SEQ ID NO:1 under hybridization conditions of 5×SSC at 42° C. for 12 hours followed by wash conditions of 5×SSC at 42° C. for 1 hour, under conditions that enable expression of the nucleic acid molecule to produce menthone: (3R)-(−)-menthol reductase in the host cell. In the practice of some embodiments of the methods of this aspect of the invention, the nucleic acid molecule that encodes a menthone: (3R)-(−)-menthol reductase hybridizes to the complement of SEQ ID NO:1 under hybridization conditions of 5×SSC at 55° C. for 12 hours, followed by wash conditions of 5×SSC at 55° C. for 1 hour. In the practice of some embodiments of the methods of this aspect of the invention, the nucleic acid molecule that encodes a menthone: (3R)-(−)-menthol reductase hybridizes to the complement of SEQ ID NO:1 under hybridization conditions of 5×SSC at 65° C. for 12 hours, followed by wash conditions of 5×SSC at 65° C. for 1 hour.

In the practice of the methods of the invention for increasing the amount of a menthone: (3R)-(−)-menthol reductase in a host cell (e.g., a plant cell), an expression vector can be introduced into a living cell by any useful means, such as any of the representative techniques described supra. An expression vector of the present invention can be introduced into one, or more, individual living cells, and whole organisms (e.g., plants) may be regenerated therefrom to yield organisms in which the level of menthone: (3R)-(−)-menthol reductase is increased.

In another aspect, the present invention provides isolated menthone: (3R)-(−)-menthol reductases that are each at least 70% identical to the amino acid sequence of the menthone: (3R)-(−)-menthol reductase set forth in SEQ ID NO:2. Some isolated menthone: (3R)-(−)-menthol reductases of this aspect of the invention are at least 80% identical to the menthone: (3R)-(−)-menthol reductase protein having the amino acid sequence set forth in SEQ ID NO:2. Some isolated menthone: (3R)-(−)-menthol reductases of this aspect of the invention are at least 90% identical to the menthone: (3R)-(−)-menthol reductase protein having the amino acid sequence set forth in SEQ ID NO:2. Some isolated menthone: (3R)-(−)-menthol reductases of this aspect of the invention are at least 95% identical to the menthone: (3R)-(−)-menthol reductase protein having the amino acid sequence set forth in SEQ ID NO:2. Some isolated menthone: (3R)-(−)-menthol reductases of this aspect of the invention are at least 99% identical to the menthone: (3R)-(−)-menthol reductase protein having the amino acid sequence set forth in SEQ ID NO:2.

The term "percent identity" or "percent identical", is the percentage of amino acid residues in a candidate polypeptide sequence that are identical with a subject polypeptide sequence (e.g., SEQ ID NO:2) after aligning the candidate and subject sequences to achieve the maximum percent identity. When making the comparison, gaps are introduced into the candidate sequence in order to achieve the best alignment with the subject sequence. Percentage identity can be determined using version 10 of the GAP computer program which is sold, as part of the GCG package of programs, by Accelrys, Inc., San Diego, Calif., U.S.A. GAP uses the algorithm of Needleman & Wunsch *J. Mol. Biol.* 48:443-53 (1970). The default gap creation penalty value of 10, and gap extension penalty value of 2, are used.

The proteins of the present invention can be isolated, for example, by incorporating an isolated nucleic acid molecule of the invention (such as a cDNA molecule) into an expression vector, introducing the expression vector into a host cell (e.g., cultured plant cells, or yeast cells) and expressing the nucleic acid molecule to yield protein. The protein can then be purified by art-recognized means. When a crude protein extract is initially prepared, it may be desirable to include one or more proteinase inhibitors in the extract. Representative examples of proteinase inhibitors include: serine proteinase inhibitors (such as phenylmethylsulfonyl fluoride (PMSF), benzamide, benzamidine HCl, ε-Amino-n-caproic acid and aprotinin (Trasylol)); cysteine proteinase inhibitors, such as sodium p-hydroxymercuribenzoate; competitive proteinase inhibitors, such as antipain and leupeptin; covalent proteinase inhibitors, such as iodoacetate and N-ethylmaleimide; aspartate (acidic) proteinase inhibitors, such as pepstatin and diazoacetylnorleucine methyl ester (DAN); metalloproteinase inhibitors, such as EGTA [ethylene glycol bis(β-aminoethyl ether) N,N,N',N'-tetraacetic acid], and the chelator 1,10-phenanthroline.

Representative examples of art-recognized techniques for purifying, or partially purifying, proteins from biological material are exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of protein and/or peptide purification, hydrophobic interaction chromatography depends on surface hydrophobic groups and is carried out under conditions which maintain the integrity of the protein molecule. Reversed-phase chromatography depends on the native hydrophobicity of the protein and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding proteins at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that is often applied to the purification of proteins is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish bandspreading, and (3) the columns are operated at 10-60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography. Art-recognized techniques for the purification of proteins and peptides are set forth in *Methods in Enzymology*, Vol. 182, Guide to Protein Purification, Murray P. Deutscher, ed. (1990), which publication is incorporated herein by reference. In particular, Section IV, chapter 14, of the Deutscher publication discloses representative techniques for the preparation of protein extracts from plant material.

A representative procedure for isolating menthone: (3R)-(−)-menthol reductase (SEQ ID NO:2), from *E. coli* expressing a cDNA (SEQ ID NO:1) encoding menthone: (3R)-(−)-menthol reductase (SEQ ID NO:2), is set forth in Example 1 herein.

In addition to native proteins, protein variants produced by deletions, substitutions, mutations and/or insertions are intended to be within the scope of the invention except insofar as limited by the prior art. The protein variants of this invention may be constructed by mutating the DNA sequences that encode the wild-type proteins, such as by using techniques commonly referred to as site-directed mutagenesis. Nucleic acid molecules encoding the proteins of the present invention can be mutated by a variety of PCR techniques well known to one of ordinary skill in the art. (See, for example, the following publications, the cited portions of which are incorporated by reference herein: *PCR Strategies*, M. A. Innis et al. eds., 1995, Academic Press, San Diego, Calif. (Chapter 14); *PCR Protocols: A Guide to Methods and Applications*, M. A. Innis et al. eds., Academic Press, N.Y. (1990).)

By way of non-limiting example, the two primer system used in the Transformer Site-Directed Mutagenesis kit from Clontech (Palo Alto, Calif.), may be employed for introducing site-directed mutants into nucleic acid molecules that encode proteins of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker, Sanford, Me.) to confirm that no other alterations in the sequence have occurred (by band shift comparison to the unmutagenized control).

Again, by way of non-limiting example, the two primer system utilized in the QuikChange™ Site-Directed Mutagenesis kit from Stratagene (LaJolla, Calif.), may be employed for introducing site-directed mutations into nucleic acid molecules that encode proteins of the present invention. Double-stranded plasmid DNA, containing the insert bearing the target mutation site, is denatured and mixed with two oligonucleotides complementary to each of the strands of the plasmid DNA at the target mutation site. The annealed oligonucleotide primers are extended using Pfu DNA polymerase, thereby generating a mutated plasmid containing staggered nicks. After temperature cycling, the unmutated, parental DNA template is digested with restriction enzyme DpnI which cleaves methylated or hemimethylated DNA, but which does not cleave unmethylated DNA. The parental, template DNA is almost always methylated or hemimethylated since most strains of *E. coli*, from which the template DNA is obtained, contain the required methylase activity. The remaining, annealed vector DNA incorporating the desired mutation(s) is transformed into *E. coli*.

Nucleic acid molecules encoding proteins of the present invention (including variants of the naturally-occurring proteins) can be cloned into an expression vector that can be employed to transform *E. coli* for high level production of the protein, and purification by standard protocols. Examples of plasmid vectors and *E. coli* strains that can be used to express high levels of the proteins of the present invention are set forth in Sambrook et al., *Molecular Cloning, A Laboratory Manual*, 2nd Edition (1989), Chapter 17.

Other site directed mutagenesis techniques may also be employed with the nucleotide sequences of the invention. For example, restriction endonuclease digestion of DNA followed by ligation may be used to generate deletion variants of proteins of the present invention, as described in section 15.3 of Sambrook et al. *Molecular Cloning: A Laboratory Manual*, 2nd Ed., Cold Spring Harbor Laboratory Press, New York, N.Y. (1989), incorporated herein by reference. A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183, 1983); Sambrook et al., supra; *Current Protocols in Molecular Biology*, 1991, Wiley (NY), F. T. Ausubel et al. eds., incorporated herein by reference.

Generally, oligonucleotides of at least 25 nucleotides in length are used to insert, delete or substitute two or more nucleotides in a nucleic acid molecule encoding a protein of the invention. An optimal oligonucleotide will have 12 to 15 perfectly matched nucleotides on either side of the nucleotides coding for the mutation. To mutagenize a wild-type protein, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type synthase inserted in the vector, and the second strand of DNA encodes the mutated form of the synthase inserted into the same vector. This heteroduplex molecule is then transformed into a suitable host cell.

Mutants with more than one amino acid substituted may be generated in one of several ways. For example, if the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding wild-type protein is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Eukaryotic expression systems may be utilized for the production of proteins of the invention since they are capable of carrying out any required posttranslational modifications and of directing the proteins to the proper cellular compartment. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* (1986); Luckow et al., *Bio-technology* 6:47-55, 1987) for expression of the proteins of the invention. Infection of insect cells (such as cells of the species *Spodoptera frugiperda*) with the recombinant baculoviruses allows for the production of large amounts of proteins. In addition, the baculovirus system has other important advantages for the production of recombinant proteins. For example, baculoviruses do not infect humans and can therefore be safely handled in large quantities. In the baculovirus system, a DNA construct is prepared including a vector and a DNA segment encoding a protein. The vector may comprise the polyhedron gene promoter region of a baculovirus, the baculovirus flanking sequences necessary for proper cross-over during recombination (the flanking sequences comprise about 200-300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/protein combination is flanked on both sides by 200-300 base pairs of baculovirus DNA (the flanking sequences).

To produce the desired DNA construct, a cDNA clone encoding the full length protein is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full-length protein. For example, an insect host cell can be cotransfected or transfected separately with the DNA construct and a functional baculovirus. Resulting recombinant baculoviruses can then be isolated and used to infect cells to effect production of the protein. Host insect cells include, for example, *Spodoptera frugiperda* cells, that are capable of producing a baculovirus-expressed protein. Insect host cells infected with a recombinant baculovirus of the present invention are then cultured under conditions allowing expression of the baculovirus-encoded protein. Protein thus produced is then extracted from the cells using methods known in the art.

Other eukaryotic microbes such as yeasts may also be used to express the proteins of the present invention. The baker's yeast *Saccharomyces cerevisiae*, is a commonly used yeast, although several other strains are available. The plasmid YRp7 (Stinchcomb et al., *Nature* 282:39, 1979; Kingsman et al., *Gene* 7:141, 1979; Tschemper et al., *Gene* 10:157, 1980, is commonly used as an expression vector in *Saccharomyces*. This plasmid contains the trp1 gene that provides a selection marker for a mutant strain of yeast lacking the ability to grow in tryptophan, such as strains ATCC No. 44,076 and PEP4-1 (Jones, *Genetics*, 85:12, 1977). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929, 1978. Additional yeast transformation protocols are set forth in Gietz et al., *N.A.R.* 20(17):1425, 1992; Reeves et al., *FEMS* 99(2-3):193-197, 1992, both of which publications are incorporated herein by reference.

Suitable promoting sequences in yeast vectors include the promoters for 3-phosphoglycerate kinase (Hitzeman et al., *J. Biol. Chem.* 255:2073, 1980 or other glycolytic enzymes (Hess et al., *J. Adv. Enzyme Reg.* 7:149, 1968; Holland et al., *Biochemistry* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable. Cell cultures derived from multicellular organisms, such as plants, may be used as hosts to practice this invention. Transgenic plants can be obtained, for example, by transferring plasmids that encode a protein of the invention and a selectable marker gene into plant cells and regenerating plants therefrom. Representative methods for introducing nucleic acid molecules into plant cells are described supra.

A nucleic acid molecule encoding a protein of the present invention can be incorporated into a plant along with a necessary promoter which is inducible. In the practice of this embodiment of the invention, a promoter that only responds to a specific external or internal stimulus is joined to the target cDNA. Thus, the nucleic acid molecule will not be transcribed except in response to the specific stimulus. As long as the nucleic acid molecule is not being transcribed, its protein product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235-243, 1986). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a gene of the present invention that previously has had its native promoter removed. This engineered gene is the combination of a promoter that responds to an external chemical stimulus and a gene responsible for successful production of a protein of the present invention.

In another aspect, the present invention provides methods for isolating menthone: (3R)-(−)-menthol reductase protein. The methods of this aspect of the invention include the steps of isolating menthone: (3R)-(−)-menthol reductase protein from host cells that include an expression vector that includes a nucleic acid molecule that encodes a menthone: (3R)-(−)-menthol reductase and that hybridizes to the complement of the nucleic acid molecule having the sequence set forth in SEQ ID NO:1 under hybridization conditions of 5×SSC at 42° C. for 12 hours, followed by wash conditions of 5×SSC at 42° C. for 1 hour. Some expression vectors used in the practice of this aspect of the invention include a nucleic acid molecule that encodes a menthone: (3R)-(−)-menthol reductase and hybridizes to the complement of the nucleic acid molecule having the sequence set forth in SEQ ID NO:1 under hybridization conditions of 5×SSC at 55° C. for 12 hours, followed by wash conditions of 5×SSC at 55° C. for 1 hour. Some expression vectors used in the practice of this aspect of the invention include a nucleic acid molecule that encodes a menthone: (3R)-(−)-menthol reductase and hybridizes to the complement of the nucleic acid molecule having the sequence set forth in SEQ ID NO:1 under hybridization conditions of 5×SSC at 65° C. for 12 hours, followed by wash conditions of 5×SSC at 65° C. for 1 hour. The host cells express the encoded menthone: (3R)-(−)-menthol reductase. The host cells can be cultured in vitro (e.g., a liquid culture of prokaryotic cells, or yeast cells), or can be in the form of whole transgenic plants, such as transgenic peppermint plants that include an expression vector of the present invention.

Some embodiments of the methods of this aspect of the invention include the steps of: (a) expressing within a host cell an expression vector comprising a nucleic acid molecule that encodes a menthone: (3R)-(−)-menthol reductase and that hybridizes to the complement of SEQ ID NO:1 under hybridization conditions of 5×SSC at 42° C. for 12 hours, followed by wash conditions of 5×SSC at 42° C. for 1 hour, thereby producing menthone: (3R)-(−)-menthol reductase within the host cell; and (b) isolating the expressed menthone: (3R)-(−)-menthol reductase protein from the host cell. Some nucleic acid molecules used in the practice of this aspect of the invention encode a menthone: (3R)-(−)-menthol reductase and hybridize to the complement of the nucleic acid molecule having the sequence set forth in SEQ ID NO:1 under hybridization conditions of 5×SSC at 65° C. for 12 hours, followed by wash conditions of 5×SSC at 65° C. for 1 hour.

In a further aspect, the present invention provides menthone: (3R)-(−)-menthol reductase produced by a method including the steps of: (a) expressing nucleic acid molecules, that encode a menthone: (3R)-(−)-menthol reductase, within host cells to produce menthone: (3R)-(−)-menthol reductase within the host cells, wherein the nucleic acid molecules each hybridize to the complement of SEQ ID NO:1 under hybridization conditions of 5×SSC at 42° C. for 12 hours, followed by wash conditions of 5×SSC at 42° C. for 1 hour; and (b) purifying the menthone: (3R)-(−)-menthol reductase from the host cells. In some embodiments, the menthone: (3R)-(−)-menthol reductase is produced by the foregoing method wherein the nucleic acid molecules each hybridize to the complement of SEQ ID NO:1 under hybridization conditions of 5×SSC at 65° C. for 12 hours, followed by wash conditions of 5×SSC at 55° C. for 1 hour. In some embodiments, the menthone: (3R)-(−)-menthol reductase is produced by the foregoing method wherein the nucleic acid molecules each hybridize to the complement of SEQ ID NO:1 under hybridization conditions of 5×SSC at 65° C. for 12 hours, followed by wash conditions of 5×SSC at 65° C. for 1 hour. The host cells can be any type of cells, including eukaryotic cells (e.g., plant cells, such as mint plant cells) and prokaryotic cells (e.g., bacterial cells). The host cells can be cultured in vitro (e.g., plant cell cultures), or, for example, can be part of a living organism (e.g., the menthone: (3R)-(−)-menthol reductase can be purified from transgenic plants that comprise a vector of the present invention and express menthone: (3R)-(−)-menthol reductase).

The following examples merely illustrate the best mode now contemplated for practicing the invention, but should not be construed to limit the invention. All literature citations herein are expressly incorporated by reference.

EXAMPLE 1

Cloning a Menthone: (3R)-(−)-Menthol Reductase from *M. piperita*

This Example describes the cloning of a cDNA molecule from *Mentha piperita* (peppermint) that encodes a menthone: (3R)-(−)-menthol reductase.

Plants, Enzymes, Substrates and Reagents: *Mentha×piperita* L. (cv. Black Mitcham) plants were propagated from stem cuttings and were grown in a greenhouse under previously described conditions (Gershenzon et al., *Plant Physiol* 122:205-213 (2000)). For the purpose of oil gland secretory cell isolation and oil analysis, leaves were harvested at periodic intervals for 40 days following leaf initiation. The sampling procedures have been previously described (Id.). Enzymes and reagents were obtained from New England Biochemicals (Beverly, Mass.), Promega (Madison, Wis.), Stratagene (La Jolla, Calif.), Sigma Chemical Co. (St. Louis, Mo.), Research Products International Corporation (Mt. Prospect, Ill.), Fisher Scientific (Fairlawn, N.J.) and EM Science (Gibbstown, N.J.), and were used according to the manufacturers' instructions. Substrates and standards were obtained from Haarmann and Reimer GmbH (Holzminden, Germany), Fluka Chemical Co. (Buchs, Switzerland), and Aldrich Chemical Co. (Milwaukee, Wis.), or were from the collection of Rodney B Croteau.

Oil Analysis and Product Identification: Simultaneous steam distillation and solvent extraction of 3 to 8 g samples of peppermint leaves were performed using 10 ml of pentane in a condenser-cooled Likens-Nickerson apparatus (J and W Scientific, Folsom, Calif.) as described (Ringer et al., *Arch Biochem Biophys* 418:80-92 (2003)). Microbial cultures (that expressed the target genes, as described in this Example) used for in situ feeding experiments (100 ml) were similarly distilled and extracted. Capillary GC (flame ionization detection) was used for the preliminary identification and quantification of monoterpenes, and employed a Hewlett-Packard model 5890 Series II gas chromatograph (Palo Alto, Calif.) using a 30 m×0.25 mm id fused-silica capillary column with a 0.25 µm film of polyethylene glycol ester coating (AT-1000, Alltech, Deerfield, Ill.). Cool on-column injection (40° C.) was used with programming from 40° C. to 50° C. at 40° C./min, 50° C. to 120° C. at 10° C./min, and 40° C./min to 220° C. A Hewlett-Packard 6890 Series GC-Mass Spectrometer (similar separation conditions, spectra collected at 70 eV and analyzed using Hewlett-Packard Chemstation software) was employed for product identification by comparison of retention times and mass spectra to those of authentic standards.

Oil Gland Secretory Cell Isolation: Oil gland secretory-cell isolation (as a prelude to RNA isolation) was carried out as previously described utilizing a leaf surface abrasion technique (Gershenzon et al., *Anal Biochem* 200:130-138 (1992)) and a buffer containing 0.5 M $NaHPO_4$, 0.2 M sorbitol, 10 mM sucrose, 2 mM DTT, 1% (w/v) PVP-40, 0.6% (w/v) methyl cellulose, and aurintricarboxylic acid (1 mM) and thiourea (5 mM) to inhibit RNase and phenol oxidase activities (McConkey et al., *Plant Physiol.* 122: 215-223 (2000)). Secretory cell clusters, largely free from contaminating mesophyll cells and nonglandular trichomes, were frozen and stored in liquid $N_2$ until use.

RNA Isolation and cDNA Preparation: Sonication of the thawed, isolated secretory cell clusters was performed in a 1:1 (v/v) mixture of the above described isolation buffer and a guanidinium-isothiocyanate-based buffer (Buffer RLT, Qiagen, Inc., Valencia, Calif.) at full power for 30 sec using the Virtis model CL4 sonicator (Virtis, Gardiner, N.Y.). Total RNA was purified using the RNeasy kit following the manufacturer's protocol (Qiagen, Inc.). Approximately 1-5 µg of total RNA and an oligo $dT_{16-20}$ were utilized as template and primer, respectively, for reverse transcription of mRNA using MMLV-reverse transcriptase (RnaseH-) following the indicated protocol (Promega, Madison, Wis.). After 1 h at 42° C., the reverse transcription reaction was heated to 68° C. for 3 min to denature RNA secondary structure, and an additional unit of the reverse transcriptase was added to the reaction mixture, which was incubated for 30 min at 42° C. Single-stranded cDNA was stored at −20° C. until use.

Cloning of a menthone: (3R)-(−)-menthol reductase: Cloning of the menthone: (3R)-(−)-menthol reductase cDNA (SEQ ID NO:1) by PCR amplification involved designing primers based on conserved regions (amino acid sequence) shared by isopiperitenone reductase and a menthone: (3S)-(+)-neomenthol reductase. The isopiperitenone reductase amino acid sequence is disclosed in Ringer et al., *Arch. Biochem. Biophys.*, 418:80-92 (2003). The nucleic acid sequence of a cDNA molecule encoding menthone: (3S)-(+)-neomenthol reductase is disclosed (as clone ML 472) in published international patent application US 01/02567, published on Jul. 26, 2001, although the identity of the protein encoded by clone ML 472 is not disclosed because its identity as a menthone: (3S)-(+)-neomenthol reductase had not been established when international patent application US 01/02567 was filed.

PCR reactions combined one of the following forward primers: 5'-GCRAACARAGGAATCGGG-3' (SEQ ID NO:3); 5'-AGGAATCGGGTTCGAAATCTGC-3' (SEQ ID NO:4); and 5'-GATATTCTGGTGAATAATGCAGGA-3' (SEQ ID NO:5) with one of the following reverse primers: 5'-GGCCCYCCATCAGGCAGCA-3' (SEQ ID NO:6); 5'-GGAATGAGGGCTTGTGTTA-3' (SEQ ID NO:7); 5'-GCTTYGTCTCGAGKGAAGAAGCA-3' (SEQ ID NO:8); and 5'-ATTTATGCRGAAACTCGGGTA-3' (SEQ ID NO:9) to amplify internal fragments of the menthone: (3R)-(−)-menthol reductase cDNA (SEQ ID NO:1). The resulting purified amplicons were cloned using topoisomerase T/A-based cloning methods (Invitrogen, Carlsbad, Calif.), and sequenced.

5'-Rapid amplification of cDNA ends (RACE) was accomplished by terminal transferase-mediated tailing of the resulting single-stranded cDNA with dCTP, and PCR amplification of the dC-tailed product using forward primer 5'-GGAAA-CAGCTATGACCATGACGGGIIGGGIIGGGIIGG-3' (SEQ ID NO:10) and one of the following gene-specific reverse primers: 5'-ATCCGAGTATACGCATTAAC-3' (SEQ ID NO:11); 5'-TTGTTGCAATTTACCATCAA-3' (SEQ ID NO:12); 5'-TTCCTCCACCTTCCCTTCAT-3' (SEQ ID NO:13); 5'-AGGCTGGAGCAGTAAGGTCGA-3' (SEQ ID NO:14); and 5'-ATTGTTGGTGAATCAGATTT-3' (SEQ ID NO:15). 3'-RACE utilized a 5'-modified oligo-dT primer, 5'-CATTATGCTGAGTGATATCCCG$(T)_{18}$-3' (SEQ ID NO:16), for reverse transcription, followed by PCR amplification using a reverse primer that annealed to the 5'-end of the newly synthesized cDNA, 5'-CATTATGCTGAGTGATATC-CCG-3' (SEQ ID NO:17), and one of the following gene-specific, internal forward primers: 5'-TGAATAATGCAG-GATTTACT-3' (SEQ ID NO:18); 5'-CTTGAGGCAAACATTATTGC-3' (SEQ ID NO:19); 5'-AACATTATTGCAGCTCAGGGTGG-3' (SEQ ID NO:20); or 5'-CCTCTCCTGCAAAAATCTGA-3' (SEQ ID NO:21). Amplification of the RT-PCR-RACE products utilized Taq DNA polymerase with the conditions described above, except that the $Mg^{2+}$ concentration was 1.5 mM and an additional 1.5 mM dATP was added to the reaction mixture during the final incubation at 72° C. The resulting amplicons were gel purified and cloned into TOPO2.1 vector according to the manufacturer's instructions (Invitrogen).

5'- and 3'-RACE clones were sequenced, and this information was utilized to design a forward primer containing a 5'-NdeI site (5'-GGAATTCCATATGGCAGATACGTTTAC-CCAA-3') (SEQ ID NO:22) and a reverse primer containing a 5'-BamHI site (5'-CGCGGATCCTTACTAGATTTAGTA-CAAGGACAAGGC-3') (SEQ ID NO:23) for PCR amplification of full-length reductase from the original cDNA. Following restriction digestion, the DNA was directionally ligated into pSBET for protein expression. N-terminal his-tagged constructs were prepared by BamHI and NdeI restriction digestion of the pSBET constructs followed by ligation into similarly digested pET-28a vector (Invitrogen). Standard procedures were followed for ligations and alkaline lysis-based plasmid preparations.

Sequencing and Bioinformatics: All clones were fully sequenced using Amplitaq DNA polymerase and fluorescence cycle sequencing using an ABI Prism 373 DNA sequencer at the Washington State University Laboratory for Biotechnology and Bioanalysis. Sequences were analyzed and aligned using the GCG 10.0 sequence analysis package (GCG, Madison, Wis.) and the ClustalX v.1.83 multiple sequence alignment program (Thompson et al., 1997), and sequence comparisons were made using the BLAST algorithm (Altschul et al., 1990) at the National Center for Biotechnology Information website. cDNAs encoding putative menthone: (3R)-(−)-menthol reductases were identified for in situ functional screening in *E. coli* as described (Ringer et al., *Arch Biochem. Biophys.* 418:80-92 (2003)).

Expression and Assay of Recombinant Menthone: (3R)-(−)-Menthol Reductase: Expression of recombinant terpene biosynthetic enzymes in *E. coli* has been described (Williams et al., *Biochemistry* 37:12213-12220 (1998)) and was carried out with the following minor changes. Bacteria harboring the pSBET-reductase plasmid or the pET-reductase plasmid were grown in 5 ml cultures of Luria-Bertani (LB) media to an $OD_{600}$ of 0.8-1.0, at which time the cultures were cooled to 10° C., isopropyl-β-D-thiogalactopyranoside was added to 0.25 mM, and growth was continued for 12-18 h at 10° C. with shaking at 220 rpm. Cells were pelleted by centrifugation for 25 min at 2500 g and 4° C., and then resuspended in 1 ml resuspension buffer (50 mM Mopso, pH 7, with 10% (v/v) glycerol, 10% (w/v) sorbitol, and 10 mM α-mercaptoethanol) containing 0.4 mg/ml lysozyme. Following incubation on ice for 30 min, the extract was sonicated for 10 sec with a Virtis sonicator using a microtip probe at medium power. Cell debris was pelleted by centrifugation at 27,000 g at 4° C. for 30 min, and the supernatant, containing the operationally soluble reductase, was used for initial characterization.

Preparative scale cultures (1.0 L) were grown and prepared essentially as described above, except that the pelleted *E. coli* cells were resuspended in 10 ml resuspension buffer and sonicated using the macrotip probe. Purification of the native reductase generated from the pSBET-reductase vector was achieved by anion exchange chromatography using Macro-Prep High Q media (Bio-Rad Corp., Hercules, Calif.); although the reductase did not bind to the matrix, significant purification was achieved and the resulting flow through and/or wash contained the reductase at ~60% purity. Purification of the N-terminal his-tagged construct utilized Ni-agarose chromatography (Qiagen, Inc.) in which the recombinant reductase bound to 3 ml of the matrix, and, following a 30 ml wash (40 mM $KH_2PO_4$, pH 7, with 0.5 M NaCl, 10 mM β-mercaptoethanol and 5 mM histidine), was eluted with a similar buffer containing 155 mM histidine to yield the reductase at >95% purity.

Preliminary assays contained 50-100 μl of the above enzyme preparation (15-50 μg protein) in 2 ml assay buffer (40 mM $KH_2PO_4$, pH 7, with 10 mM β-mercaptoethanol) containing 100 μM menthone and 500 μM NADPH. Following incubation with gentle shaking at 31° C. for 12 h, 0.5 ml of pentane was added and the mixture was vigorously mixed to extract the monoterpene products which were analyzed by GC and GC-MS as described above. In situ functional assays utilized 100 ml *E. coli* cultures that were grown and induced under the conditions described above, except that 100 μM menthone was added directly to the culture at the time of induction. Following 15 h of shaking (250 rpm) at 15-20° C., these cultures were transferred to 0.5 L round-bottom flasks, to which 6.6 μmol of (+)-camphor was added as an internal standard, and the mixture was steam distilled and the distillate analyzed as described above.

pH optimum was determined in assay buffer (pH 4 to 12 in 0.5 pH unit increments) containing 25 μM menthone and 500 μM NADPH to which 0.5 μg protein was added prior to initiation of the reaction (6 min at 31° C.) with GC-based product analysis as described above. Substrate specificity was evaluated in assay buffer containing 0.5 μg reductase at the pH optimum and 100 μM monoterpenone substrate ((−)-isopiperitenone, (+)-pulegone, (+)-cis-isopulegone, (−)-carvone or (+)-menthone) and 500 μM NADPH, or 100 μM monoterpenol substrate ((−)-menthol, (+)-isomenthol, (+)-neoisomenthol or (+)-neomenthol) and 500 μM $NADP^+$, by overnight incubation as described above.

Kinetic Analysis of Recombinant Menthone: (3R)-(−)-Menthol Reductase: Typical kinetic assays were performed essentially as described (Ringer et al., *Arch Biochem Biophys* 418:80-92 (2003)) under linear reaction conditions (with respect to protein and time) with the following changes. Assay mixtures containing 2 ml of 40 mM $KH_2PO_4$ at pH 7, with 10 mM β-mercaptoethanol were combined with 500 μM cofactor and concentrations of monoterpene substrate ranging from 2.5 μM to 1 mM, or with 100 μM monoterpene substrate, and concentrations of cofactor ranging from 0.1 μM to 1 mM, and preheated to 31° C. before initiation of the reaction by enzyme addition (0.008 to 1.3 μg protein). The reactions were quenched after 6 to 9 min by addition of 0.5 ml pentane containing camphor as internal standard (6.6 μM) followed by vigorous mixing and cooling on ice; quantitation of products in the pentane extract was achieved by capillary-GC using the conditions described above with peak area quantification using the internal standard for normalization. Protein concentration of the purified N-terminally $(his)_6$-tagged menthone: (3R)-(−)-menthol reductase was determined spectrophotometrically $(A_{280})$ using an extinction coefficient of 23260 $M^{-1}cm^{-1}$. Recombinant menthone: (3R)-(−)-menthol reductase that lacked the his-tag was quantified by densitometry following separation by SDS-PAGE and Coomassie blue (R250) staining, using the his-tagged forms as standard. Kinetic constants, representing the average of at least two independent experiments, were determined by nonlinear regression analysis of Michaelis-Menten plots using Enzyme Kinetics, v 1.11 (Trinity Software, Plymouth, N.H.). The values reported are the means±standard error.

Isolation and Characterization of a cDNA Molecule Encoding Menthone: (3R)-(−)-Menthol Reductase: Oil analyses were conducted with developing leaves of peppermint plants during a 40-day period following cutting and regrowth to identify the time during which the rate of menthol production was highest (i.e., indicative of increased transcription of the target reductase). The rate of menthol accumulation was maximum from 25 to 33 days post leaf initiation, with increases of about 2% menthol (relative to the total oil) per day; maximum menthol levels (~25% of total oil) were reached by 40 days. Therefore, secretory cell clusters were isolated from fully expanded leaves 25 days post emergence, and RNA was extracted, purified and used for cDNA synthesis.

PCR amplification of the cDNA (synthesized from mRNA isolated from mature oil glands) generated an ~525 bp gene fragment. 5'-RACE and 3'-RACE were used to obtain a partial length cDNA molecule which provided nucleic acid sequence from the 5'- and 3'-termini included 59 and 104 base pairs of the respective untranslated regions, and which facilitated amplification of the complete open reading frame of the cDNA (SEQ ID NO:1) and provide restriction sites for transfer into the expression vectors, pSBET and pET28a. PCR amplification from the 5'-RACE cDNA pool yielded a long clone (SEQ ID NO:1) and a short clone. The short clone lacked menthone: (3R)-(−)-menthol reductase activity and was not characterized further.

In vitro Demonstration of Menthone Reductase Activity: The menthone: (3R)-(−)-menthol reductase cDNA clone (SEQ ID NO:1) was expressed in *E. coli*, and the resulting partially purified recombinant protein (SEQ ID NO:2) was assayed for menthone reductase activity. The recombinant protein (SEQ ID NO:2) was functional and, in the presence of NADPH, produced 95% (3R)-(−)-menthol and 5% (3S)-(+)-neomenthol from (−)-menthone, and 87% (3R)-(+)-neoisomenthol and 13% (3S)-(+)-isomenthol from (+)-isomenthone, thus confirming that this clone (SEQ ID NO:1) encodes a menthone: (3R)-(−)-menthol reductase; the identity of the enzyme products were verified by GC-MS analysis.

Sequence Analysis and Enzyme Characterization: the cDNA clone having the sequence set forth in SEQ ID NO:1 encodes a 311 residue protein (SEQ ID NO:2) with a deduced molecular weight of 34,070. The apparent absence of N-terminal organellar targeting information is consistent with a cytoplasmic localization for the enzyme.

The reductase (SEQ ID NO:2) exhibited a broad pH response curve, with the pH optimum at 7.0 with half maximal activities at pH 4.5 and 8.5. Of the alternate substrates tested ((−)-isopiperitenone, (+)-cis-isopulegone, (+)-pulegone, (+)-menthone and (−)-carvone), the reductase (SEQ ID NO:2) was only able to detectably reduce (+)-menthone to the corresponding monoterpenols. NADH served as a much less efficient cofactor than NADPH (less than 20% turnover at saturation under linear reaction conditions) but the stereochemical fidelity of the reduction reaction was maintained.

Non-linear regression analysis of Michaelis-Menten plots was used to obtain $K_m$ values and turnover numbers for the menthone: (3R)-(−)-menthol reductase (SEQ ID NO:2), expressed from pSBET, for menthone and NADPH as cosubstrates (see Table 1).

TABLE I

Kinetic parameters for the menthone: menthol reductase (SEQ ID NO: 2).

| $K_m$ (μM) | | | | | |
|---|---|---|---|---|---|
| menthone[a] | isomenthone[a] | NADPH[b] | neomenthol[c] | NADP+[d] | $k_{cat}$ (sec$^{-1}$)[e] |
| 3.0 ± 0.6 | 41 ± 5 | 0.12 ± 0.04 | N.D.[f] | N.D.[f] | 0.6 |

Assays to determine $K_m$ values utilized:
[a]NADPH as cofactor;
[b]menthone as substrate;
[c]NADP+ as cofactor; and
[d]neomenthol as substrate.
[e]Turnover numbers were determined using menthone and NADPH.
[f]N.D. indicates the values were not determined.

EXAMPLE 2

Genetic Transformation of Peppermint

This procedure for genetically transforming peppermint (*Mentha×piperita* L.) is based on the procedure set forth in Niu et al., *Plant Cell Reports* 17:165-171, 1998, which publication is incorporated herein by reference.

Plant material and explant sources: in vitro shoot cultures of peppermint (*Mentha×piperita* L. var. Black Mitcham) plants are initiated from rhizome explants of peppermint plants maintained in a greenhouse. Shoots are obtained by stimulating axillary bud development from these explants. Typically, 3 to 6 weeks after initial culture shoots are of sufficient size to be used as leaf explants for regeneration or transformation experiments, or to be recultured for continued shoot proliferation.

Tissue culture and plant regeneration: Rhizome segments (1 cm) are surface disinfected in a solution of 20% bleach (1.05% sodium hypochlorite) with Tween-20 (1 ml/liter of solution) for 20 min and then washed with sterile deionized water. The segments are placed onto the surface of a medium including the following basal constituents: Murashige and Skoog (MS) salts (*Physiol. Plant* 15:473-497, 1962), 100 mg/liter myo-inositol, 0.4 mg/liter thiamine, 7.5 g/liter bacteriological grade agar, 30 g/liter sucrose, and 0.1 mg/liter N benzyladenine (BA). The medium should be adjusted to pH 5.8 prior to autoclave sterilization. Typically, shoots will elongate from the axillary buds in the rhizome after 3-4 weeks of culture. Shoots about 1 cm in height are recultured onto the same medium at 3- to 4-week intervals. Shoots (about 5-8 cm in height), at the end of a culture passage, are the source of leaf explants for genetic transformation.

Leaves (1 cm or less in length), including portions of the petioles, are excised from the proximal 5-cm region of the shoot. The leaves should be excised horizontally and the edges of the basal portion trimmed. These explants are placed onto the surface of shoot regeneration medium that contains the basal constituents and 25% coconut water, plus a cytokinin (pH 5.8). Thidiazuron is preferably utilized as a cytokinin for organogenesis. Explants or, subsequently, calli are typically recultured at 2 week intervals. Callus develops about 5 weeks after culture initiation and shoots are visible shortly thereafter.

For shoot elongation and root initiation, isolated shoots (6-7 mm) are cultured onto rooting medium that contains the basal constituents and 0.01 mg/liter α-naphthaleneacetic acid (pH 5.8). Shoots are recultured every 2 weeks. Two culture passages are required for sufficient shoot elongation and two to three additional passages for sufficient root development to permit successful soil transplantation. Plants in soil are moved either to a growth chamber or a greenhouse and humidity should be gradually reduced to facilitate hardening.

Shoot cultures used as explant sources, or shoots in elongation or rooting stages of culture, are maintained at 26° C. and 16 h photoperiod at 25 μmol m$^{-2}$s$^{-1}$. Leaf explants on regeneration medium are maintained in darkness at 26 C.

*Agrobacterium* transformation and kanamycin selection: Representative *A. tumefaciens* strains useful for genetically transforming peppermint are LBA 4404 (Hoekema et al., *Nature* 303:179-180, 1983) and EHA 105 (Hood et al., *Transgen. Res.* 2:208-218, 1993). A representative binary vector plasmid useful for transforming peppermint is pBISN 1 (Narasimhulu et al., *Plant Cell* 8:873-886, 1996). This binary vector contains a neomycin phosphotransferase (nptII) marker gene for kanamycin selection. *Agrobacterium* strains can be grown at 30° C. on AB-sucrose minimal or YEP agar medium with 50 μg/ml of kanamycin and 10 μg/ml of rifampicin.

An overnight culture (5 ml YEP medium with 25 mg/liter kanamycin, 28° C.) is inoculated with a single *Agrobacterium* colony isolated from a freshly cultured plate. An aliquot of this culture is used to inoculate a new 50 ml culture that is grown at 28° C. for 3-4 hours to an $OD_{600}$ of 1.0. Entire leaves are submerged into *Agrobacterium* culture solution and basal portions (with petiole segments) are excised. Explants are additionally wounded by dissecting away the remaining margins of the leaf piece. The leaf explants are then incubated in the bacterial solution for 30 minutes, blotted briefly, and placed onto regeneration medium without antibiotics for a 4- to 5-day cocultivation period in darkness at 26° C. After cocultivation, the explants are washed with sterile water and then transferred to regeneration medium containing 2.0 mg/liter (8.4 µM) thidiazuron with 20 mg/liter kanamycin and 200 mg/liter Ticaricillin (SmithKline Beecham Pharmaceuticals, Philadelphia, Pa.) for selection of transformed plant cells and inhibition of bacteria, respectively. Shoot elongation and rooting medium contains 15 mg/liter kanamycin and 100 mg/liter Ticar.

Shoot regeneration of peppermint plants from leaf explants: leaves from the proximal 5 cm of the shoot are most morphogenetically responsive for adventitious shoot formation. Further, explants from the basal portion of the leaf contain cells with greater organogenetic competence than those in the leaf tip. Organogenesis occurs either directly from cells in the explant or from those in primary callus. Temporally, shoot or primary callus formation occurs rather uniformly from regions of the leaf that have been injured as a consequence of dissection during explant preparation.

BA, zeatin, or 2-iP have been determined to be required for adventitious shoot formation from orange mint explants (Van Eck and Kitto 1990, 1992). Of the cytokinins tested, thidiazuron most effectively induces shoot formation from cells in peppermint leaf explants. Further, thidiazuron suppresses adventitious root formation that occurs naturally from cultured explants.

When roots have formed, plantlets are transferred to potting soil in small covered glass jars in a low light, high humidity, low temperature, growth chamber. Over the course of 10 days, and with frequent watering, the jars are gradually uncovered to permit complete air exchange. At this time, roots and shoots are sufficiently well developed to permit transfer to soil in larger pots in a greenhouse.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule that hybridizes to the complement of SEQ ID NO: 1 under hybridization conditions of 5×SSC at 65° C. for 12 hours, followed by wash conditions of 5×SSC at 65° C. for 1 hour.

2. A replicable expression vector that comprises a nucleic acid molecule that hybridizes to the complement of SEQ ID NO:1 under hybridization conditions of 5×SSC at 65° C. for 12 hours, followed by wash conditions of 5×SSC at 65° C. for 1 hour.

3. A host cell comprising an expression vector that comprises a nucleic acid molecule that hybridizes to the complement of SEQ ID) NO:1 under hybridization conditions of 5×SSC at 65° C. for 12 hours, followed by wash conditions of 5×SSC at 65° C. for 1 hour.

4. A host cell of claim 3 wherein the host cell is a eukaryotic cell,

5. A host cell of claim 3 wherein the host cell is a prokaryotic cell.

6. A host cell of claim 3, wherein the host cell is a plant cell.

7. A host cell of claim 3, wherein the host cell is from a plant of the genus Mentha.

8. A host cell of claim 3, wherein the host cell is from Mentha piperita.

9. A transgenic plant comprising an expression vector that comprises a nucleic acid molecule that hybridizes to the complement of SEQ ID NO:1 under hybridization conditions of 5×SSC at 65° C. for 12 hours, followed by wash conditions of 5×SSC at 65° C. for 1 hour.

10. A transgenic plant of claim 9 wherein the transgenic plant is a member of the genus Mentha.

11. A transgenic plant of claim 9 wherein the transgenic plant is a member of the species Mentha piperita.

12. A method of increasing the amount of a menthone: (3R)-(−)-menthol reductase in a host cell, the method comprising the step of introducing into a host cell an expression vector comprising a nucleic acid molecule that hybridizes to the complement of SEQ ID NO:1 under hybridization conditions of 5×SSC at 65° C. for 12 hours, followed by wash conditions of 5×SSC at 65° C. for 1 hour, under conditions that enable expression of the nucleic acid molecule to produce menthone:(3R)-(−)-menthol reductase.

13. The method of claim 12, wherein the host cell is a plant cell.

14. The isolated nucleic acid molecule of claim 1, wherein the isolated nucleic acid comprises the sequence set forth in SEQ ID NO:1.

15. An isolated nucleic acid molecule that encodes a polypeptide with at least 90% amino acid sequence identity to SEQ ID NO:2.

* * * * *

UNITED STATES PATENT AND TRADEMARK OFFICE
CERTIFICATE OF CORRECTION

PATENT NO.       : 8,426,684 B2
APPLICATION NO.  : 11/569493
DATED            : April 23, 2013
INVENTOR(S)      : R. B. Croteau et al.

Page 1 of 1

It is certified that error appears in the above-identified patent and that said Letters Patent is hereby corrected as shown below:

In the Claims:

| COLUMN | LINE | ERROR |
|---|---|---|
| 35 (Claim 3, line 3) | 61 | "ID)" should read --ID-- |
| 35 (Claim 4, line 2) | 65 | "cell," should read --cell.-- |

Signed and Sealed this
Twenty-second Day of October, 2013

Teresa Stanek Rea
*Deputy Director of the United States Patent and Trademark Office*

SEQUENCE LISTING

```
<160> NUMBER OF SEQ ID NOS: 23

<210> SEQ ID NO 1
<211> LENGTH: 1096
<212> TYPE: DNA
<213> ORGANISM: Mentha Piperita
<220> FEATURE:
<221> NAME/KEY: CDS
<222> LOCATION: (60)..(992)

<400> SEQUENCE: 1
agtgtgtata caaataagca aaaaaaatct ccttaattaa agacacaaca agcaaaaaa        59 atg gca gat acg ttt acc caa agg tat gct ttg gtt act ggt gca aac       107
Met Ala Asp Thr Phe Thr Gln Arg Tyr Ala Leu Val Thr Gly Ala Asn
1               5                   10                  15 aaa gga atc ggg ttc gag ata tgc agg cag tta gct tcg aaa gga atg       155
Lys Gly Ile Gly Phe Glu Ile Cys Arg Gln Leu Ala Ser Lys Gly Met
            20                  25                  30 aag gtg att tta gct tca aga aac gag aag aga ggc atc gaa gct cga       203
Lys Val Ile Leu Ala Ser Arg Asn Glu Lys Arg Gly Ile Glu Ala Arg
        35                  40                  45 gaa agg cta ctt aag gag tcg aga tca att tct gat gac gat gtt gtt       251
Glu Arg Leu Leu Lys Glu Ser Arg Ser Ile Ser Asp Asp Asp Val Val
    50                  55                  60 ttt cat caa ctc gat gtt gct gac cct gct agc gct gtt gct gtt gct       299
Phe His Gln Leu Asp Val Ala Asp Pro Ala Ser Ala Val Ala Val Ala
65                  70                  75                  80 cac ttc atc gaa acc aaa ttc ggg agg ctt gat att ctg gtg aat aat       347
His Phe Ile Glu Thr Lys Phe Gly Arg Leu Asp Ile Leu Val Asn Asn
                85                  90                  95 gcg gga ttt act gga gta gcg ata gag gga gat att tca gtg tat caa       395
Ala Gly Phe Thr Gly Val Ala Ile Glu Gly Asp Ile Ser Val Tyr Gln
            100                 105                 110 gag tgt ctt gag gca aac att att gca gct cag ggt gga cag gca cat       443
Glu Cys Leu Glu Ala Asn Ile Ile Ala Ala Gln Gly Gly Gln Ala His
        115                 120                 125 cca ttc cat ccc aaa act act ggt agg ctg att gag aca ttg gag ggt       491
Pro Phe His Pro Lys Thr Thr Gly Arg Leu Ile Glu Thr Leu Glu Gly
    130                 135                 140
```

-continued

| | | |
|---|---|---|
| tca aaa gag tgt ata gaa aca aac tac tat ggc aca aaa aga ata aca<br>Ser Lys Glu Cys Ile Glu Thr Asn Tyr Tyr Gly Thr Lys Arg Ile Thr<br>145                   150                  155                 160 | 539 |
| gaa acc cta att cct ctc ctg caa aaa tct gat tca cca aca att gtc<br>Glu Thr Leu Ile Pro Leu Leu Gln Lys Ser Asp Ser Pro Thr Ile Val<br>                  165                  170                  175 | 587 |
| aat gtc tcc tcc acc ttc tcg act tta ctg ctc cag cct aat gaa tgg<br>Asn Val Ser Ser Thr Phe Ser Thr Leu Leu Leu Gln Pro Asn Glu Trp<br>             180                  185                 190 | 635 |
| gca aaa gga gtg ttt agc agc aac agc ctg aat gaa ggg aag gtg gag<br>Ala Lys Gly Val Phe Ser Ser Asn Ser Leu Asn Glu Gly Lys Val Glu<br>         195                  200                 205 | 683 |
| gaa gtt ttg cat gaa ttt ctc aag gat ttc att gat ggt aaa ttg caa<br>Glu Val Leu His Glu Phe Leu Lys Asp Phe Ile Asp Gly Lys Leu Gln<br>210                   215                  220 | 731 |
| caa aac cac tgg cct cct aac ttt gca gcc tac aaa gta tcg aaa gct<br>Gln Asn His Trp Pro Pro Asn Phe Ala Ala Tyr Lys Val Ser Lys Ala<br>225                   230                  235                 240 | 779 |
| gct gtt aat gcg tat act cgg atc ata gcg cga aag tac ccg agt ttc<br>Ala Val Asn Ala Tyr Thr Arg Ile Ile Ala Arg Lys Tyr Pro Ser Phe<br>                  245                  250                  255 | 827 |
| tgc ata aat tca gtg tgt cct ggt ttt gtt aga aca gat att tgc tac<br>Cys Ile Asn Ser Val Cys Pro Gly Phe Val Arg Thr Asp Ile Cys Tyr<br>         260                  265                 270 | 875 |
| aat ctt gga gta cta agt gaa gct gaa ggt gct gaa gct ccg gtg aag<br>Asn Leu Gly Val Leu Ser Glu Ala Glu Gly Ala Glu Ala Pro Val Lys<br>275                   280                  285 | 923 |
| ctg gct ttg ttg ccc gat ggc ggg ccc tcg ggc tcc ttt ttc tct cga<br>Leu Ala Leu Leu Pro Asp Gly Gly Pro Ser Gly Ser Phe Phe Ser Arg<br>         290                  295                 300 | 971 |
| gag gaa gcc ttg tcc ttg tac taaatcaaag agaaccacc accaaacccc<br>Glu Glu Ala Leu Ser Leu Tyr<br>305                 310 | 1022 |
| atgctaaggt ctttatcaat gggcttttta ttataccatg gtagtaaaaa taaaattaaa | 1082 |
| tggggtttgg aatg | 1096 |

<210> SEQ ID NO 2
<211> LENGTH: 311
<212> TYPE: PRT
<213> ORGANISM: Mentha Piperita

<400> SEQUENCE: 2

Met Ala Asp Thr Phe Thr Gln Arg Tyr Ala Leu Val Thr Gly Ala Asn
1               5                   10                  15

Lys Gly Ile Gly Phe Glu Ile Cys Arg Gln Leu Ala Ser Lys Gly Met
               20                   25                   30

Lys Val Ile Leu Ala Ser Arg Asn Glu Lys Arg Gly Ile Glu Ala Arg
             35                   40                   45

Glu Arg Leu Leu Lys Glu Ser Arg Ser Ile Ser Asp Asp Val Val
        50                  55                   60

Phe His Gln Leu Asp Val Ala Asp Pro Ala Ser Val Ala Val Ala
65                70                  75                   80

His Phe Ile Glu Thr Lys Phe Gly Arg Leu Asp Ile Leu Val Asn Asn
                 85                   90                   95

Ala Gly Phe Thr Gly Val Ala Ile Glu Gly Asp Ile Ser Val Tyr Gln
               100                  105                 110

Glu Cys Leu Glu Ala Asn Ile Ile Ala Ala Gln Gly Gly Gln Ala His
         115                  120                 125

```
Pro Phe His Pro Lys Thr Thr Gly Arg Leu Ile Glu Thr Leu Glu Gly
    130                 135                 140

Ser Lys Glu Cys Ile Glu Thr Asn Tyr Tyr Gly Thr Lys Arg Ile Thr
145                 150                 155                 160

Glu Thr Leu Ile Pro Leu Leu Gln Lys Ser Asp Ser Pro Thr Ile Val
                165                 170                 175

Asn Val Ser Ser Thr Phe Ser Thr Leu Leu Leu Gln Pro Asn Glu Trp
            180                 185                 190

Ala Lys Gly Val Phe Ser Ser Asn Ser Leu Asn Glu Gly Lys Val Glu
            195                 200                 205

Glu Val Leu His Glu Phe Leu Lys Asp Phe Ile Asp Gly Lys Leu Gln
210                 215                 220

Gln Asn His Trp Pro Pro Asn Phe Ala Ala Tyr Lys Val Ser Lys Ala
225                 230                 235                 240

Ala Val Asn Ala Tyr Thr Arg Ile Ile Ala Arg Lys Tyr Pro Ser Phe
                245                 250                 255

Cys Ile Asn Ser Val Cys Pro Gly Phe Val Arg Thr Asp Ile Cys Tyr
            260                 265                 270

Asn Leu Gly Val Leu Ser Glu Ala Glu Gly Ala Glu Ala Pro Val Lys
            275                 280                 285

Leu Ala Leu Leu Pro Asp Gly Gly Pro Ser Gly Ser Phe Phe Ser Arg
        290                 295                 300

Glu Glu Ala Leu Ser Leu Tyr
305                 310

<210> SEQ ID NO 3
<211> LENGTH: 18
<212> TYPE: DNA
<213> ORGANISM: Artificial Sequence
<220> FEATURE:
<223> OTHER INFORMATION: Oligonecleotide

<400> SEQUENCE: 3
gcraacarag gaatcggg                                                      18

<210> SEQ ID NO 4
<211> LENGTH: 22
<212> TYPE: DNA
<213> ORGANISM: Artificial Sequence
<220> FEATURE:
<223> OTHER INFORMATION: Oligonecleotide

<400> SEQUENCE: 4
aggaatcggg ttcgaaatct gc                                                 22

<210> SEQ ID NO 5
<211> LENGTH: 24
<212> TYPE: DNA
<213> ORGANISM: Artificial Sequence
<220> FEATURE:
<223> OTHER INFORMATION: Oligonecleotide

<400> SEQUENCE: 5
gatattctgg tgaataatgc agga                                               24

<210> SEQ ID NO 6
<211> LENGTH: 19
<212> TYPE: DNA
<213> ORGANISM: Artificial Sequence
<220> FEATURE:
<223> OTHER INFORMATION: Oligonecleotide
```

```
<400> SEQUENCE: 6
ggcccyccat caggcagca                                                    19

<210> SEQ ID NO 7
<211> LENGTH: 19
<212> TYPE: DNA
<213> ORGANISM: Artificial Sequence
<220> FEATURE:
<223> OTHER INFORMATION: Oligonecleotide

<400> SEQUENCE: 7
ggaatgaggg cttgtgtta                                                    19

<210> SEQ ID NO 8
<211> LENGTH: 23
<212> TYPE: DNA
<213> ORGANISM: Artificial Sequence
<220> FEATURE:
<223> OTHER INFORMATION: Oligonecleotide

<400> SEQUENCE: 8
gcttygtctc gagkgaagaa gca                                               23

<210> SEQ ID NO 9
<211> LENGTH: 21
<212> TYPE: DNA
<213> ORGANISM: Artificial Sequence
<220> FEATURE:
<223> OTHER INFORMATION: Oligonecleotide

<400> SEQUENCE: 9
atttatgcrg aaactcgggt a                                                 21

<210> SEQ ID NO 10
<211> LENGTH: 38
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(38)
<223> OTHER INFORMATION: Wherein N in positions 25, 26, 30, 31, 35 and
      36 = Inosine

<400> SEQUENCE: 10
ggaaacagct atgaccatga cgggnngggn ngggnngg                               38

<210> SEQ ID NO 11
<211> LENGTH: 20
<212> TYPE: DNA
<213> ORGANISM: Artificial Sequence
<220> FEATURE:
<223> OTHER INFORMATION: Oligonecleotide

<400> SEQUENCE: 11
atccgagtat acgcattaac                                                   20

<210> SEQ ID NO 12
<211> LENGTH: 20
<212> TYPE: DNA
<213> ORGANISM: Artificial Sequence
<220> FEATURE:
<223> OTHER INFORMATION: Oligonecleotide

<400> SEQUENCE: 12
```

```
ttgttgcaat ttaccatcaa                                               20

<210> SEQ ID NO 13
<211> LENGTH: 20
<212> TYPE: DNA
<213> ORGANISM: Artificial Sequence
<220> FEATURE:
<223> OTHER INFORMATION: Oligonecleotide

<400> SEQUENCE: 13
ttcctccacc ttcccttcat                                               20

<210> SEQ ID NO 14
<211> LENGTH: 21
<212> TYPE: DNA
<213> ORGANISM: Artificial Sequence
<220> FEATURE:
<223> OTHER INFORMATION: Oligonecleotide

<400> SEQUENCE: 14
aggctggagc agtaaggtcg a                                             21

<210> SEQ ID NO 15
<211> LENGTH: 20
<212> TYPE: DNA
<213> ORGANISM: Artificial Sequence
<220> FEATURE:
<223> OTHER INFORMATION: Oligonecleotide

<400> SEQUENCE: 15
attgttggtg aatcagattt                                               20

<210> SEQ ID NO 16
<211> LENGTH: 23
<212> TYPE: DNA
<213> ORGANISM: Artificial Sequence
<220> FEATURE:
<223> OTHER INFORMATION: Oligonecleotide

<400> SEQUENCE: 16
cattatgctg agtgatatcc cgt                                           23

<210> SEQ ID NO 17
<211> LENGTH: 22
<212> TYPE: DNA
<213> ORGANISM: Artificial Sequence
<220> FEATURE:
<223> OTHER INFORMATION: Oligonecleotide

<400> SEQUENCE: 17
cattatgctg agtgatatcc cg                                            22

<210> SEQ ID NO 18
<211> LENGTH: 20
<212> TYPE: DNA
<213> ORGANISM: Artificial Sequence
<220> FEATURE:
<223> OTHER INFORMATION: Oligonecleotide

<400> SEQUENCE: 18
tgaataatgc aggatttact                                               20

<210> SEQ ID NO 19
<211> LENGTH: 20
<212> TYPE: DNA
<213> ORGANISM: Artificial Sequence
<220> FEATURE:
```

-continued

```
<223> OTHER INFORMATION: Oligonecleotide

<400> SEQUENCE: 19
cttgaggcaa acattattgc                                               20

<210> SEQ ID NO 20
<211> LENGTH: 23
<212> TYPE: DNA
<213> ORGANISM: Artificial Sequence
<220> FEATURE:
<223> OTHER INFORMATION: Oligonecleotide

<400> SEQUENCE: 20
aacattattg cagctcaggg tgg                                           23

<210> SEQ ID NO 21
<211> LENGTH: 20
<212> TYPE: DNA
<213> ORGANISM: Artificial Sequence
<220> FEATURE:
<223> OTHER INFORMATION: Oligonecleotide

<400> SEQUENCE: 21
cctctcctgc aaaaatctga                                               20

<210> SEQ ID NO 22
<211> LENGTH: 31
<212> TYPE: DNA
<213> ORGANISM: Artificial Sequence
<220> FEATURE:
<223> OTHER INFORMATION: Oligonecleotide

<400> SEQUENCE: 22
ggaattccat atggcagata cgtttaccca a                                  31

<210> SEQ ID NO 23
<211> LENGTH: 36
<212> TYPE: DNA
<213> ORGANISM: Artificial Sequence
<220> FEATURE:
<223> OTHER INFORMATION: Oligonecleotide

<400> SEQUENCE: 23
cgcggatcct tactagattt agtacaagga caaggc                             36
```